United States Patent [19]
Viola

[11] 3,962,150
[45] June 8, 1976

[54] FOAM PRODUCING CLEANSING COMPOSITIONS

[75] Inventor: Leonard J. Viola, Yonkers, N.Y.

[73] Assignee: Richardson-Merrell Inc., Wilton, Conn.

[22] Filed: Apr. 10, 1974

[21] Appl. No.: 459,651

[52] U.S. Cl. ............................... 252/542; 252/153; 252/546; 252/547; 252/DIG. 1; 252/DIG. 5; 424/78; 424/309
[51] Int. Cl.² ........................................... C11D 1/58
[58] Field of Search ............... 252/DIG. 5, 153, 542, 252/557, 546, DIG. 1; 424/78, 309

[56] References Cited
UNITED STATES PATENTS

| | | | |
|---|---|---|---|
| 3,131,152 | 4/1964 | Klausner | 252/DIG. 5 |
| 3,131,153 | 4/1964 | Klausner | 252/DIG. 5 |
| 3,370,014 | 2/1968 | Reich et al. | 252/DIG. 5 |
| 3,533,955 | 10/1970 | Pader et al. | 252/153 |
| 3,580,853 | 5/1971 | Parran | 252/DIG. 5 |
| 3,862,965 | 1/1975 | Werner et al. | 252/557 X |

*Primary Examiner*—Thomas J. Herbert, Jr.
*Attorney, Agent, or Firm*—William J. Stein; Eugene O. Retter; George W. Rauchfuss, Jr.

[57] ABSTRACT

An aqueous skin cleansing composition is described suitable for use as a non-pressurized, aerated, low-density foam cleanser.

10 Claims, No Drawings

FOAM PRODUCING CLEANSING COMPOSITIONS

FIELD OF THE INVENTION

This invention relates to novel aqueous compositions useful as skin cleaners. Additionally, these compositions possess certain physical characteristics which enable them to be dispensed as non-pressurized, aerated, low density foams for use in personal care products.

BACKGROUND OF THE INVENTION

Soaps, detergents and abrasives have long been used to cleanse the skin on various portions of the body. One practical disadvantage to their use, however, is the fairly large amounts of water required for cleansing purposes and for the removal of residual cleansing agents. More recently, waterless cleansers have come into vogue. However, they have the disadvantage of leaving a residual film upon the surface of the skin after cleansing.

There is a great need for a convenient means for cleansing the skin which will efficiently cleanse, which does not require large volumes of water for cleansing, and which will not result in a residual film being left on the surface of the skin after cleansing. Such a skin cleanser is particularly useful wherever water is not readily available as for example when traveling or camping. On the other hand, the use of copious amounts of water may not always be practical. For example, when practicing personal hygiene in the vaginal, anal or perianal regions of the body, the present practice is to use dry, absorbent toilet paper. The use of copious amounts of water, as in a bidet, which is widely practiced in many parts of Europe and South America, has never received widespread acceptance in this country. The use of absorbent paper only does not always result in an efficient cleansing of the body leaving a tendency to smear rather than effecting a good cleansing effect upon the surrounding areas. Furthermore, irrespective of how soft the paper may be, vigorous rubbing frequently produces an abrasive effect which bruises and disrupts the sensitive tissues in this area, thereby increasing the likelihood for subsequent bacterial infection to occur.

I have discovered certain novel, aqueous surfactant compositions with particular physical properties that readily enable the preparation of stable non-pressurized, aerated foams. These foams possess good cleansing power and detergency, are mild and non-irritating, and leave little, if any, residual film remaining on the cleansed surface of the skin. These compositions are homogeneous in nature, can be structured to be wet or dry, stable or fastbreaking, and are esthetically suitable for use in a wide variety of personal care products.

One of the principal purposes of this invention is to describe the preparation of an aqueous skin cleansing composition which will produce a usable foam from a hand-held squeezable, foam dispensing device.

Another object of the present invention is to provide liquid compositions which can be varied so as to produce uniform wet or dry foams.

Another object of this invention is to provide foam-producing compositions which produce relatively stable or collapsible foams. A preferred embodiment of this invention is to provide skin cleansing foams of low density that are pressure-sensitive which readily break or collapse under slight pressure.

Another object of this invention is to provide a foam-producing composition whose wetting characteristics are such as to enable its use as a cleansing agent in conjunction with disposable facial or toilet tissue and not cause the tissue to tear and break.

Another object of this invention is to provide a foam which is mild and non-irritating and which does not require the use of propellants, thereby avoiding the danger of explosion or corrosion of the container.

Still another object of this invention is to provide a foam producing composition such that if placed in a hand-held, foam dispensing device having deformable walls, the amount of force required to produce the foam is not excessive and is readily usable by the average person.

These objectives as well as others apparent to those skilled in the art are obtained with the foam-producing compositions described herein.

SUMMARY OF THE INVENTION

This invention relates to a novel, aqueous, foam-producing skin cleansing composition which comprises a total surfactant composition of from 1 to 15% having from 0.5 to 14.5% by weight of a nonionic surfactant and from 0.5 to 14.5% by weight of an anionic surfactant; from 1.0 to 15.0% of an alcoholic solvent selected from the group consisting of monohydric alcohols having from 2 to 3 carbon atoms, glycol ethers, polyhydric glycols and mixtures thereof; and from 70 to 98% by weight of water; said composition having a viscosity of from 0.5 to 300 cps and a surface tension of from 20 to 70 dynes/cm at room temperature; said composition when suitably mixed with air will produce a foam having a density of from 0.01 to 0.10 gm/ml.

Additionally, this invention relates to an aqueous, non-pressurized, aerated foam consisting of a mixture of the composition with air, said foam having a density of from 0.01 to 0.10 gm/ml.

DETAILED DESCRIPTION OF THE INVENTION

The essence of the present invention lies in the discovery that a narrow concentration range of certain combinations of surfactants, when dissolved in water containing a water-miscible alcoholic solvent will produce an aqueous, non-pressurized, aerated foam suitable for cleansing of the skin. Furthermore, this invention describes a range of effective concentrations which can be employed to produce foams that are either coarse and wet which quickly flatten, or foams that are soft, containing fine bubbles and which are relatively dry having long foam stability.

The principal active ingredients of the compositions are the combinations of surfactants which are employed. Suitable surfactants include a variety of foam-producing anionic, cationic and nonionic surfactants. In the practice of this invention, however, one of the principal considerations in the selection of a suitable surfactant is whether or not the particular surfactant is toxic or causes irritation to the skin, particularly when exposed to damaged skin, such as with cuts or bruises. The use of non-allergenic surfactants is particularly desirable for people having allergenic responses and sensitive skin.

Suitable anionic surfactants which can be employed include the long alkyl chain sulfonates such as the alkyl sodium sulfosuccinates, the sulfoacetates, alcohol ethoxylated sulfates, alkane sulfonates, alkyl aryl sulfonates, alkyl phenol ethoxylated sulfates, amide sulfonates, petroleum sulfonates and amphoteric type surfactants such as the imidazolines, alkyl betaines, and alkanoyl sarcosinate fatty acids.

Suitable cationic surfactants which can be employed in lieu of an anionic surfactant include the germicide and non-germicide type of compounds. In addition to cetyl trimethyl ammonium bromide and hydroxide, one may use several other quaternaries, e.g., cetyl dimethyl benzyl ammonium chloride, cetyl dimethyl ethyl ammonium bromide, lauryl dimethyl benzyl ammonium chloride, dimethyl didecenyl ammonium chloride, laurylisoquinolinium bromide, N-soya N-ethyl morpholinium sulfate, cetyl trimethyl ammonium stearate, lauryl dimethyl benzyl dimethyl ammonium chloride, octadecenyl-9-dimethyl ethyl ammonium bromide, diisobutyl cresoxy ethoxy ethyldimethylbenzyl ammonium chloride, diisobutylphenoxyethoxy ethyldimethylbenzyl ammonium chloride, octadecyl dimethyl ethyl ammonium bromide, stearyl dimethyl benzyl ammonium chloride, cetyl pyridinium chloride, and cetyl pyridinium bromide.

The surfactants of choice in the present invention, however, are the nonionic surfactants due to their pharmacological compatability, stability, and due to their lack of irritation and toxicity. Suitable nonionic surfactants include the polyoxyethylene-polyoxypropylene block polymers, alkyl polyoxyethylene, alkyl sorbitan polyoxyethylene, and alkyl aryl polyoxyethylene polymers, alkylamine oxides, acetylenic glycols, fatty acid amides and polyglyceryl fatty acid esters.

The preferred nonionic surfactants are the polyoxyethylene-polyoxypropylene block polymers. More particularly, the preferred surfactants are polyoxyethylene-polyoxypropylene block polymers which have a molecular weight of from 1,000 to 17,000 and in which the total amount of the hydrophilic group ranges from 10 to 80% of polyoxyethylene polymer and the total amount of the hydrophobic group ranges from 90 to 20% of polyoxypropylene polymer. These surfactants may be liquids, semi-solids or solids, thereby providing a wide range of balanced physical properties. By judiciously selecting the concentration, molecular weight and ratio of polyoxyethylene to polyoxypropylene polymers, such composition parameters as water solubility, low hygroscopicity, low order of toxicity and irritation and such foam composition parameters as breaking speed, pressure sensitivity, wettability and foam density can be controlled.

Thus, for example, increased water solubility of these polymers is a function of decreasing molecular weight and a minimum content of the polyoxypropylene hydrophobe. Conversely, maximum wetting properties are obtained with maximum molecular weight polymers with a maximum content of the polyoxypropylene hydrophobe. Maximum detergency is shown by compositions containing approximately equal proportions of the polyoxyethylene hydrophile with polyoxypropylene hydrophobe and having molecular weights ranging from 2500 to 4500. Maximum foaming properties are shown by compositions containing approximately 40–70% of the polyoxyethylene hydrophile polymer with an average molecular weight ranging from 4000 to 8000.

As can be seen no one particular blend of polyoxyethylene-polyoxypropylene block polymers is best suited for all purposes and one of the principal features of my invention is to enable the formulation of a variety of compositions possessing different characteristics suitable for different purposes. Thus, for example, where a coarse wet foam which rapidly flattens is desired as in an otological preparation, a blend of 80% polyoxyethylene hydrophile polymer — 20% polyoxypropylene hydrophobe polymer having an average molecular weight of 8000–8500 can be employed. Alternatively, where a more stable wet foam is desired, as for example, on the hairy surfaces of the skin, a blend of 40% polyoxyethylene hydrophile polymer — 60% polyoxypropylene hydrophobe polymer having an average molecular weight of 2000–2500 is employed. For general skin cleansing purposes a foam composition comprising approximately equal parts of both the polyoxyethylene hydrophile and the polyoxypropylene hydrophobe is preferred.

Although the nonionic or anionic surfactants may be used in and of themselves to produce stable foams, I have discovered that the combination of a nonionic surfactant with an anionic surfactant will provide compositions possessing superior properties. Such compositions generally demonstrate an increased foamability and will produce more uniform and stable foam compositions whose wetting characteristics and foam densities can be carefully blended or regulated. In general, the nonionic blends of polyoxyethylene-polyoxypropylene block polymers are preferred due to their versatility and their lack of toxicity and irritation. The preferred anionic surfactants employed are the large molecular weight N-acyl derivatives of sarcosine, such as N-lauroyl sarcosinate. Still more particularly, the commercially available colorless 30% solution of the neutral sodium salt of N-lauroyl sarcosinate is preferred because of its neutrality and because it produces stable foams having a low density. Compositions containing these surfactants do not leave an oily residue on the surface of the skin which tend to clog the sebaceous glands of the skin. The lack of an oily residue on the skin surface has the further advantage of not staining clothing, particularly when being applied to the perianal or vaginal areas of the body.

The amount of the surfactants employed includes from about 0.5 to 14.5% of a nonionic surfactant and from about 0.5 to 14.5% of an anionic surfactant. All of the percentages expressed herein are as a percent weight per 100 ml. of solution volume. The total amount of surfactant employed in the compositions of this invention ranges from about 1.0 to about 15.0%. A preferred concentration of total surfactant ranges from 3.0 to 9.0% with a distribution of nonionic to anionic surfactants having a ratio ranging from about 9:1 to about 0.1:1. A preferred embodiment of this invention contains a mixture of 2 nonionic polyoxyethylene-polyoxypropylene block polymers in combination with an anionic N-acyl sarcosine surfactant as illustrated by the composition described in Example 1.

The following table illustrates the various types of typical foams obtained using representative nonionic and anionic surfactants. In this table surfacant A is a blend of 80% polyoxyethylene hydrophile block polymer and 20% polyoxypropylene hydrophobe block polymer, having an average molecular weight of 8350; surfactant B is a blend of 40% polyoxyethylene hydrophile block polymer and 60% polyoxypropylene hydrophobe block polymer, having an average molecular weight of 2200; and surfactant C is the anionic surfactant, sodium lauroyl-sarcosinate.

TABLE I

WETTABILITY AND FOAM DENSITIES

| Surfactant | % Surfactant in Distilled Water | Wettability | Foam Density (g/ml) |
|---|---|---|---|
| A | 0.10 | loose, coarse bubbles, wet foam, quickly flattens | 0.2857 |
| A | 0.50 | loose, coarse, bubbles, wet foam, quickly flattens | 0.2000 |
| A | 1.25 | uniform foam, wet, quickly flattens | 0.2000 |
| B | 0.10 | loose, wet foam | 0.2286 |
| B | 0.50 | wet foam | 0.1429 |
| B | 1.25 | wet foam | 0.1714 |
| Combination A & B | 1.25% (A) 1.25% (B) | very wet foam | 0.1714 |
| C (at pH 7.6) | 0.45 | dry, uniform foam | 0.0286 |
| C (at pH 6.3) | 0.15 | dry, uniform foam | 0.0571 |
| Combination A & B & C (Example 1) | 1.25% (A) 1.25% (B) 1.50% (C) | good, uniform foam with good wettability | 0.0286 |

It was experimentally found that the foam-breaking qualities of these compositions could be better controlled using water soluble or water dispersible compounds in combination with an alcoholic co-solvent rather than in using oil soluble compounds with water alone. The term alcoholic solvent refers to a water-miscible co-solvent component. This co-solvent component is selected from the group consisting of monohydric alcohols having from 2 to 3 carbon atoms, such as ethanol and isopropanol, glycol ethers, such as polyoxyethylene having a molecular weight of from about 400 to about 20,000, and alkylpolyoxyethylene having a molecular weight of from about 300 to 2500, and polyhydric glycols such as propylene glycol, glycerin, 1,2,6-hexanetriol, 1,3-hexanediol and dipropylene glycol. The preferred embodiment illustrated in Example 1 of this invention contains a combination of 4% propylene glycol and 2% glycerin, which produces a uniform, white foam that is stable when placed on cleansing tissue or toilet paper, that is pressure sensitive and rapidly flattens, and that will not clog the discharge orifice even after continuous usage.

Additional minor components can be added to the compositions of this invention in order to increase their attractiveness, versatility and shelf-life. Perfumes or water soluble, pharmaceutically acceptable dyes or food colors can be added to enhance the attractiveness of these compositions. Antifungal and antimicrobial agents are useful in preventing mold or bacterial contamination and in increasing the shelf-life of the compositions. A combination of methyl and propyl parabens has been found to be particularly useful for this purpose. For general purposes skin cleansing compositions having a pH range of from about 5.0 to 8.0 are desirable. If necessary, the pH of these compositions can be adjusted downward using lactic acid. For skin cleansers which deal with more sensitive skin surfaces, such as in vaginal and perianal cleansers, a pH of about 6.5 is desirable. These and other minor modifications can be made without materially altering or departing from the basic concept of this invention.

The nature of the foam produced determines the usefulness of the present compositions. In order for a foam to be useful as a skin cleansing agent, it must have a uniform consistency, good spreadability, good cleansing ability, and be pressure sensitive, i.e., have rapid breaking power when pressure is applied. In addition, when used in conjunction with facial or toilet tissue the foam must not be so wet as to cause the tissue to tear and shred, nor can the foam be so dry as to prevent flattening under pressure. Finally, a skin cleansing foam must be esthetically acceptable. I have discovered that all of these properties are met by keeping the aqueous skin cleaning compositions described herein within certain parameters of viscosity and surface tension.

In order to produce a non-pressurized aerated foam from a hand-held foam producing device, such as described in U.S. Pat. No. 3,709,437, a minimum applied force of about 15 psi is required. This amount of force is the lower limit of squeezability required by the average consumer to produce a suitable foam. To produce a skin cleansing foam with this low amount of force, the viscosity of the composition should be no less than 0.5 and no more than 100 cps on the Brookfield Viscometer, Model No. LVT or RVT. Preferably, a Shirley Ferrante Viscometer is used for more accurate viscosity measurements at a high sheer rate of 300 rpm. When used in this fashion, a viscosity of from 0.5 to 50 cps is required for the instant compositions with a viscosity of 15 cps or less deemed optimum for a general skin cleansing composition. At high viscosities foams become very aerated and the force necessary to extrude them from a foam dispensing device becomes unreasonably great.

The foamability and wettability characteristics are governed by the surface tension of the skin cleansing composition. The surface tension for the compositions of this invention varies from about 20 to 70 dynes/cm. For general skin cleansing compositions a range of from about 23 to about 50 dynes/cm is preferred. Liquid compositions having a surface tension in the lower portion of this range possess greater spreading and better wetting characteristics with increased foamability. Foamable compositions having higher surface tensions generally provide more stable foams but are also more difficult to cause to foam and require more force to extrude the foam. Beyond 50 dynes/cm, the foams obtained are very wet and cause tissue shredding.

The foam-producing skin cleansing compositions of this invention are particularly advantageous in that they leave a minimum amount of surfactant residue on the surface of the skin. This has been achieved in part by utilizing a low percentage of total surfactants in the skin cleansing composition itself, and by preparing foams with unusually low density. The present compositions provide foam densities in the range of from 0.01 to 0.10 g/ml. These foam densities provide good cleansing ability and more importantly, leave a negligible amount of surfactant residue on the surface of the skin upon flattening. Above these values, very wet foams that cause tearing and shredding of tissue are obtained, whereas foams produced below these values are too thin and airy to be of any practicable use. If deposited onto an absorbent tissue such as a facial tissue, toilet tissue or onto the skin itself, the foams of this invention remain stable for a period of 1 to 2 minutes, breaking down only very slowly. If, however, slight pressure is applied by rubbing onto the skin or rubbing onto the paper, the foams rapidly break down without leaving a sticky or tacky residue and are said to be "pressure sensitive."

The cleansing ability of these aerated foams is a direct function of the cleansing ability of the surfactant solution itself which produces the foam. In order to determine surfactant cleansing ability the following test system was developed, which effectively measures soil removal from swatches of fabric. Synthetic soil is prepared consisting of 50 parts by weight of U.S.P. lanolin, 48 parts by weight of light mineral oil, 1 part by weight of methylcellulose 15 cps (Methocel MC) and 1 part by weight of carbon black. One gram of this synthetic soil or one gram of pooled, sterile and dried human feces is added to and spread upon individual 1⅞ inch diameter, double-napped cotton pads. These pads, including controls, are dried to a constant weight and added to 50 ml of the test surfactant solution contained in a Burrell Wrist Action Shaker. After a specified period the pads are dried and reweighed. The percent soil removed in this fashion is indicated in the following chart wherein A represents sodium lauroyl sarcosinate, B represents a blend of 80% polyoxyethylene-20% polyoxypropylene block polymers having an average molecular weight of 8350, and C represents sodium coconut imidazoline dicaboxylate.

TABLE II

| Feces | % SOIL REMOVED Compositions | | | | | | | |
|---|---|---|---|---|---|---|---|---|
| | 3% A | 3% A | 5% A | 9% A | 1% B | 3% B | 5% B | 5% C |
| pH (Adjusted) 1 min shaker | 6.1 | 6.8 | 6.1 | 6.8 | 6.0 | 6.0 | 6.1 | 6.0 |
| (% Removed) 5 min shaker | 39.5 | 39.7 | 28.0 | 34.0 | 61.0 | 53.0 | 35.5 | 13.5 |
| (% Removed) Lanolin Soil | 76.0 | 78.2 | 79.4 | 77.7 | — | 74.0 | 65.6 | 30.0 |
| pH (Adjusted) 5 min shaker | 6.1 | 6.8 | 6.1 | 6.8 | 6.0 | 6.0 | 6.1 | 6.0 |
| (% Removed) | 11.5 | 20.8 | 9.5 | 38.0 | 69.5 | — | 63.6 | 8.0 |

In order to conveniently produce the foams of this invention a suitable non-pressurized foam dispensing container such as described in U.S. Pat. No. 3,709,437 can be employed. The composition is placed into the reservoir of a plastic squeeze bottle which contains a foamer head or a foam producing means. Squeezing the container causes the solution to leave the reservoir and enter an air-mixing or foaming chamber via an internal dip tube. The foam produced in the foaming chamber is generally passed through a homogenizing element interposed between the air-mixing chamber and the discharge orifice to homogenize and control the consistency of the discharged foam. Further compression of the side walls of the squeeze bottle discharges the foam from a discharge cap as a uniform non-pressurized aerated foam.

The skin cleansing compositions described herein are more particularly illustrated in conjunction with the following specific Examples.

EXAMPLE I

| | Percent w/v |
|---|---|
| Nonionic polyoxyethylene (80%)-polyoxypropylene (20%) block copolymer having an average molecular weight of 8350 (PLURONIC F-68) | 1.25 |
| Nonionic polyoxyethylene (40%)-polyoxypropylene (60%) block copolymer having an average molecular weight of 2200 (PLURONIC L-44) | 1.25 |
| Sodium lauroyl sarcosinate (30% solution) | 1.50 |
| Propylene glycol | 4.00 |
| Glycerin | 2.00 |
| Methylparaben | 0.10 |
| Propylparaben | 0.05 |
| Polyoxyethylene (20) oleyl ether (BRIJ-99) | 0.40 |
| Fragrance | 0.18 |

EXAMPLE I-continued

| | Percent w/v |
|---|---|
| Lactic acid (10% solution) | 0.005–0.030 |
| Purified water q.s. ad | 100.00 ml |

The two nonionic polyoxyethylene-polyoxypropylene surfactants and sodium lauroyl sarcosinate are added to approximately 500 ml of purified water with stirring until dissolved. In a separate vessel propylene glycol and glycerin is added with stirring and warmed to about 50°C. The methyl and propyl parabens are added to the propylene glycol-glycerin mixture, and stirred until dissolved. The polyoxyethylene oleyl ether and fragrance are added to the propylene glycol-glycerin mixture, and the resulting mixture is stirred to dissolve all the ingredients, cooled to about 40°–45°C. and added to the aqueous surfactant solution. The mixture is brought to about 90% of the total volume with purified water, the pH adjusted with lactic acid to about 5.7–6.3 and brought to 100 ml q.s. ad.

Using this procedure a clear, colorless liquid is obtained which is free from haze, having a "clean" fragrance and which is suitable as an anal or perianal cleanser. Compositions prepared in this manner exhibit a surface tension of 30.7 dynes/cm; a viscosity of 2 cps as determined with a Brookfield Viscometer (No. 1 spindle) at 100 rpm; and when dispensed from a non-pressurized foam dispenser produce a homogeneous pressure-sensitive foam free of large bubbles and having a foam density of 0.029–0.47 gm/ml.

EXAMPLE 2

| | Percent w/v |
|---|---|
| Sodium Coconut Imidazoline Dicarboxylate | 3.0 |
| Propylene glycol | 1.0 |
| Glycerin | 2.0 |
| Methylparaben | 0.1 |
| Propylparaben | 0.05 |
| Fragrance | 0.03 |
| Castor oil and/or Dimethyl Polysiloxane | 0.1–0.6 |
| Lactic acid adj. to pH 6 | 0.35 |
| Distilled water q.s. ad | 100.00 ml |

Following essentially the same procedure as in Example 1, the above composition has a viscosity of 17 cps using a Brookfield RVT Viscometer (No. 1 spindle) at 100 RPM and produces a uniform dry foam having a density of 0.029 gm/ml.

EXAMPLE 3

| | Percent w/v |
|---|---|
| Sodium lauroyl sarcosinate (30% solution) | 3.33 |
| Nonionic polyoxyethylene (80%) — polyoxypropylene (20%) block copolymer having an average molecular weight of 8350 (PLURONIC F-68) | 1.50 |
| Propylene glycol | 1.00 |
| Glycerin | 2.00 |
| Methylparaben | 0.10 |
| Propylparaben | 0.05 |
| Fragrance | 0.03 |
| Lactic acid (10% solution) | 1.228 |
| Purified water q.s. ad | 100.00 ml |

Following essentially the same procedure as in Example 1, but adjusting the composition to a pH of 6.0 a composition is obtained having a viscosity of 13 cps as determined with a Brookfield RVT Viscometer (No. 1 spindle), said composition producing a light uniform foam from a non-pressurized foam dispenser having a foam density of 0.034 gm/ml.

EXAMPLE 4

| | Percent w/v |
|---|---|
| Nonionic polyoxyethylene (80%)-polyoxypropylene (20%) block copolymer having an average molecular weight of 8350 (PLURONIC F-68) | 1.25 |
| Nonionic polyoxyethylene (40%)-polyoxypropylene (60%) block copolymer having an average molecular weight of 2200 (PLURONIC L-44) | 1.25 |
| Sodium Tridecyl Imidazoline Dicarboxylate (MIRANOL — 2MHT) | 10.00 |
| Propylene glycol | 4.00 |
| Glycerin | 2.00 |
| Methylparaben | 0.10 |
| Propylparaben | 0.05 |
| Polyoxyethylene (20) oleyl ether (BRIJ-99) | 0.40 |
| Fragrance | 0.18 |
| Lactic acid (10% solution) | 1.92 |
| Purified water q.s. ad | 100.00 ml |

Following essentially the same procedure of Example 1, a composition is obtained which is suitable for cleansing baby bottoms, having a surface tension of 29.5 dynes/cm and a viscosity of 16 cps as determined with a Brookfield RVT Viscometer (No. 1 spindle) at 100 rpm. When dispensed as a foam from a non-pressurized foam dispenser a dry, uniform foam is obtained having a foam density of 0.030 gm/ml.

EXAMPLE 5

| | Percent w/v |
|---|---|
| Nonionic polyoxyethylene (40%) — polyoxypropylene (60%) block copolymer having an average molecular weight of 2200 (PLURONIC L-44) | 0.50 |
| Sodium Tridecyl Imidazoline Dicarboxylate (MIRANOL-2MHT) | 14.70 |
| Propylene glycol | 4.00 |
| Glycerine | 2.00 |
| Methylparaben | 0.10 |
| Propylparaben | 0.05 |
| Polyoxyethylene (20) oleyl ether (BRIJ-99) | 0.40 |
| Fragrance | 0.18 |
| Lactic acid (10% solution) | 0.005–0.030 |
| Purified water q.s. ad. | 100.00 ml |

Following essentially the procedure of Example 1 a composition is obtained having a surface tension of 30.0 dynes/cm and a viscosity of 55 cps as determined with a Brookfield Viscometer (No. 1 spindle) at 100 RPM. When dispensed as a foam from a non-pressurized foam dispenser a very dry, tight-bubble foam is obtained which is not very pressure sensitive, i.e., it collapses only slowly under pressure.

EXAMPLE 6

| | Percent w/v |
|---|---|
| Nonionic polyoxyethylene (40%)-polyoxypropylene (60%) block copolymer having an average molecular weight of 2200 (PLURONIC L-44) | 14.50 |
| Sodium lauroyl sarcosinate (30% solution) | 0.50 |
| Propylene glycol | 4.00 |
| Glycerin | 2.00 |
| Methylparaben | 0.10 |
| Propylparaben | 0.05 |
| Polyoxyethylene (20) oleyl ether (BRIJ-99) | 0.40 |
| Fragrance | 0.18 |
| Lactic acid (10% solution) | 0.005–0.030 |
| Purified water q.s. ad. | 100.00 ml |

Following essentially the procedure of Example 1 a composition is obtained which produces a wet, slowly-collapsible foam. The composition has a surface tension of 35.5 dynes/cm and a viscosity of 20 cps as determined with a Brookfield Viscometer (No. 1 spindle) at 100 rpm. When dispensed as a foam from a non-pressurized foam dispenser, a very fine-bubbled foam is obtained having a foam density of 0.094 g/ml.

EXAMPLE 7

| | Percent w/v |
|---|---|
| Polyoxyethylene (20) sorbitan monostearate | 2.50 |
| Sodium lauroyl sarcosinate (30% solution) | 1.50 |
| Propylene glycol | 4.00 |
| Glycerin | 2.00 |
| Methylparaben | 0.10 |
| Propylparaben | 0.05 |
| Polyoxyethylene (20) oleyl ether (BRIJ-99) | 0.40 |
| Fragrance | 0.18 |
| Lactic acid (10% solution) | 0.005–0.030 |
| Purified water q.s. ad. | 100.00 ml |

Following essentially the procedure of Example 1, a composition is obtained having a surface tension of 31.3 dynes/cm and a viscosity of 12 cps as determined with a Brookfield Viscometer (No. 1 spindle) at 100 rpm. When dispensed as a foam from a non-pressurized foam dispenser a dry, uniformly tight-bubble foam is obtained which is pressure sensitive and has a foam density of 0.054 g/ml.

I claim:

1. An aqueous, non-pressurized, foam-producing, homogenous, skin-cleansing composition consisting essentially of from 0.5 to 14.5% of a pharmaceutically acceptable nonionic surfactant and from 0.5 to 14.5% of a pharmaceutically aceptable anionic surfactant, the total surfactant concentration ranging from 1 anionic to 15%; from 1 to 15% of an alcoholic solvent selected from the group consisting of monohydric alcohols having from 2 to 3 carbon atoms, glycol ethers, polyhydric glycols and mixtures thereof; and from 70 to 98% water.

2. A composition of claim 1 having a viscosity of from 0.5 to 100 cps and a surface tension of from 20 to 70 dynes/cm at room temperature.

3. A composition according to claim 1 wherein the alcoholic solvent is a mixture of from 1.0 to 4.0% of propylene glycol and from 1.0 to 3.0% of glycerine.

4. A composition according to claim 1 wherein the nonionic surfactant is a blend of polyoxyethylene and polyoxypropylene block polymers.

5. A composition according to claim 3 wherein the anionic surfactant is sodium N-lauroyl sarcosinate.

6. A composition according to claim 3 wherein the anionic surfactant is sodium tridecyl imidazoline dicarboxylate.

7. An aqueous, foam-producing, skin-cleansing composition consisting essentially of:
  a. from 2.0 to 3.0% weight/vol of a blend of polyoxyethylene and polyoxypropylene block polymers,
  b. from 0.25 to 0.75% weight/vol of a large molecular weight derivative of N-acyl-sarcosine,
  c. propylene glycol — 4% weight/vol,
  d. glycerine — 2% weight/vol, and
  e. water ad. q.s. 100.0 said composition having a viscosity at room temperature of from 1 to 20 cps, a surface tension at room temperature of from 20 to 35 dynes/cm and a pH of from 5.5 to 6.5, and which when mixed with air produces a foam having a density of 0.01 to 0.02 gm/ml.

8. An aqueous, non-pressurized, aerated foam consisting essentially of a mixture of air and an aqueous, non-pressurized, foam-producing, homogeneous, skin-cleansing composition having from 0.5 to 14.5% of a pharmaceutically acceptable nonionic surfactant and from 0.5 to 14.5% of a pharmaceutically acceptable anionic surfactant, the total surfactant concentration ranging from 1 to 15%, from 1 to 15% of an alcoholic solvent selected from the group consisting of monohydric alcohols having from 2 to 3 carbon atoms, glycol ethers, polyhydric glycols and mixtures thereof, and from 70 to 98% water; said foam having a density of from 0.01 to 0.10 gm/ml.

9. An aerated foam according to claim 8 wherein the nonionic surfactant is a blend of polyoxyethylene and polyoxypropylene block polymers.

10. An aerated foam according to claim 9 wherein the anionic surfactant is a large molecular weight derivative of N-acyl-sarcosine.

* * * * *

UNITED STATES PATENT AND TRADEMARK OFFICE
CERTIFICATE OF CORRECTION

PATENT NO. : 3,962,150
DATED : June 8, 1976
INVENTOR(S) : Leonard J. Viola

It is certified that error appears in the above–identified patent and that said Letters Patent are hereby corrected as shown below:

Column 6, line 24, "high" should read "higher"; Column 7, line 19, "dicaboxylate" should read "dicarboxylate"; Column 10, lines 63-64, "from 1 anionic to 15%" should read "from 1 to 15%"

Signed and Sealed this

Thirty-first Day of May 1977

[SEAL]

Attest:

RUTH C. MASON
*Attesting Officer*

C. MARSHALL DANN
*Commissioner of Patents and Trademarks*